US00PP22715P2

(12) United States Plant Patent
Mehlenbacher

(10) Patent No.: US PP22,715 P2
(45) Date of Patent: May 8, 2012

(54) ***CORYLUS* PLANT NAMED 'TONDA PACIFICA'**

(50) Latin Name: *Corylus avellana*
Varietal Denomination: Tonda Pacifica

(75) Inventor: Shawn A. Mehlenbacher, Corvallis, OR (US)

(73) Assignee: The State of Oregon, Acting by & Through the State Board of Higher Education, Orgeon State University, Corvallis, OR (US)

( * ) Notice: Subject to any disclaimer, the term of this patent is extended or adjusted under 35 U.S.C. 154(b) by 0 days.

(21) Appl. No.: 12/928,688

(22) Filed: Dec. 16, 2010

(51) Int. Cl.
*A01H 5/00* (2006.01)

(52) U.S. Cl. ..... Plt./152

(58) Field of Classification Search ..... Plt./152
See application file for complete search history.

*Primary Examiner* — Annette Para

(74) *Attorney, Agent, or Firm* — Dann, Dorfman, Herrell & Skillman; Robert C. Netter, Jr.

(57) ABSTRACT

A new and distinct cultivar of *Corylus* plant named 'Tonda Pacifica' is provided.

2 Drawing Sheets

Latin name of the genus and species of the plant claimed: *Corylus avellana.*

Variety denomination: 'Tonda Pacifica'.

BACKGROUND OF THE INVENTION

The present invention relates to a new and distinct cultivar of *Corylus* plant (hazelnut, filbert), botanically known as *Corylus avellana*, and hereinafter referred to by the name 'Tonda Pacifica.'

The new *Corylus* resulted from a controlled cross of female parent 'Tonda Gentile delle Langhe' and male parent OSU 23.024 made in 1981 by Maxine M. Thompson. Neither parent was protected by a plant patent. Hybrid seeds from the cross were harvested in August 1981, stratified, and seedlings grown in the greenhouse during the summer of 1982. From this cross, total of 95 seedling trees were planted in the field in Corvallis in October, 1982. 'Tonda Pacifica' was discovered and selected as a single plant within the progeny of the stated cross-pollination in a controlled environment in Corvallis, Oreg., USA. It was originally assigned the designation OSU 228.084, which indicates the row and tree location of the original seedling. 'Tonda Gentile delle Langhe' is an important cultivar in Piemonte, northern Italy. The male parent, OSU 23.024, is from a controlled cross of 'Barcelona' and 'Extra Ghiaghli'. 'Extra Ghiaghli', obtained as scions from Greece, is a clone of the important Turkish cultivar 'Tombul'.

The new cultivar was asexually reproduced by rooted suckers annually for seven years in Corvallis, Oreg. The new cultivar was also asexually propagated by whip grafting in Corvallis, Oreg. The unique features of this new *Corylus* are stable and reproduce true-to-type in successive generations of asexual reproduction.

SUMMARY OF THE INVENTION

The following traits have been observed and are determined to be the unique characteristics of 'Tonda Pacifica.' These characteristics in combination distinguish 'Tonda Pacifica' as a new and distinct cultivar:

1. Globose plant habit.
2. Yellowish-green developing and fully expanded leaves during the spring and summer.
3. Susceptibility to eastern filbert blight caused by the fungus *Anisogramma anomala* (Peck) E. Müller.
4. Absence of random amplified polymorphic DNA markers 152-800 and 268-580 in DNA of 'Tonda Pacifica' amplified by the polymerase chain reaction (PCR). These two markers are linked to a dominant allele for resistance to eastern filbert blight from the cultivar Gasaway, not patented.
5. Expression of incompatibility alleles $S_1$ and $S_2$ in the styles.
6. DNA fingerprints at 28 microsatellite marker loci differ from its parent 'Tonda Gentile delle Langhe' and grandparents 'Barcelona' and 'Extra Ghiaghli'. The microsatellite primers are shown in Table 1, and allele sizes are shown in Table 2.

Comparisons in three replicated trials conducted in Corvallis, Oreg., plants of the new *Corylus* differed from plants of the *Corylus avellena* cultivar 'Tonda Gentile delle Langhe', not patented, and other cultivars and selections of *Corylus avellena* known to the Inventors primarily in nut size, nut shape, kernel percentage (ratio of kernel weight to nut weight), frequency of blank nuts (nuts lacking kernels), time of pollen shed, time of nut maturity, length of the husk or involucre, and plant size. 'Tonda Pacifica' combines the high kernel quality of its parent 'Tonda Gentile delle Langhe' with higher yields, thinner shells, and lower susceptibility to bud mites (primarily *Phytoptus avellanae* Nal.).

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical plant of 'Tonda Pacifica' in Corvallis, Oreg.

The photograph on the second sheet shows typical nuts, raw kernels, and blanched kernels of 'Tonda Pacifica'.

DETAILED DESCRIPTION OF THE INVENTION

The cultivar 'Tonda Pacifica' has not been observed under all possible environmental conditions. The phenotype may vary somewhat with variations in environment such as temperature and light intensity, without, however, any variance in genotype. The aforementioned photographs and following observations and measurements describe plants grown in Corvallis, Oreg. under commercial practice outdoors in the field during the fall, winter, and spring. Plants used for the photographs and description were about twelve years old. In the following description, color references are made to The Royal Horticultural Society Colour Chart, 1966 Edition, except where general terms of ordinary dictionary significance are used. The following description is based on self-rooted trees growing in Corvallis, Oreg. For grafting, the rootstocks were cv. 'Montebello', not patented, propagated by tie-off layerage (stooling).

Botanical classification: *Corylus avellana* cultivar 'Tonda Pacifica.'

Parentage:

*Female, or seed, parent.*—*Corylus avellana* 'Tonda Gentile delle Langhe', not patented.

*Male, or pollen, parent.*—*Corylus avellana* selection OSU 23.024, not patented.

Propagation:

*Type*.—Rooted suckers.

*Time to initiate roots*.—About 30 days at 20° C.

*Time to produce a rooted young plant*.—About six months at 22° C.

*Root description*.—Fine to thick; freely branching; creamy white in color.

*Type*.—Whip grafting.

*Time to budbreak on the scions*.—About 14 days at 25° C.

*Time to produce a grafted plant*.—About six months at 25° C.

Plant description:

*General appearance*.—Perennial shrub. Globose plant habit, with slightly pendulous shoots.

*Growth and branching habit*.—Freely branching; about 15 lateral branches develop per plant. Pinching, i.e., removal of the terminal apices, enhances branching with lateral branches potentially forming at every node. Moderately vigorous growth habit.

*Plant height*.—About 5 meters.

*Plant diameter or spread*.—About 5 meters.

*Lateral branch description*.—Length: About 20 cm. Diameter: About 6 mm. Internode length: About 3.6 cm. Texture: Smooth, glabrous. Strength: Strong. Color, immature: 146C. Color, mature: 195A.

Foliage description:

*Arrangement*.—Alternate, simple.

*Length*.—About 11 cm.

*Width*.—About 10 cm.

*Shape*.—Oblong to ovate.

*Apex*.—Obtuse to acute.

*Base*.—Cordate.

*Margin*.—Serrate.

*Texture, upper and lower surfaces*.—Slightly pubescent.

*Venation pattern*.—Pinnate.

*Color*.—Developing foliage, upper and lower surfaces: 144A. Fully expanded foliage, upper surface: Spring and summer, 136A; late summer and fall, 136A. Fully expanded foliage, lower surface: Spring and summer, 137C; late summer and fall, 137C. Venation, upper surface: Spring and summer, 139A; late summer and fall, 139A. Venation, lower surface: Spring and summer, 139C; late summer and fall, 139C.

*Petiole*.—Length: About 11 mm. Diameter: About 1.9 mm. Texture, upper and lower surfaces: Pubescent. Color, upper surface: Spring and summer, 146D; late summer and fall, 146D. Color, lower surface: Spring and summer, 146D; late summer and fall, 146D.

Flower description: Male inflorescences are catkins, color prior to elongation 194C. Female inflorescence style color 048C.

Nuts description:

*Length*.—About 19 mm. Width: About 18 mm. Depth: About 16.5 mm. Shape: Round. Nut shape index [(Width+Depth)/2*Length]=0.91. Nut compression index (Width/Depth)=1.09. Nut shell color: 164A. Nut weight: About 2.24 grams. Kernel weight: About 1.06 grams. Kernel percentage (kernel weight/nut weight): About 47%.

Disease/pathogen/pest resistance: Plants of the new *Corylus* are susceptible to eastern filbert blight caused by the fungus *Anisogramma anomala* (Peck) E. Muller. Plants of the new *Corylus* are moderately resistant to bud mites (*Phytoptus avellanae* Nal.), while plants of 'Tonda Gentile delle Langhe' are highly susceptible, and plants of 'Barcelona' are highly resistant.

Temperature tolerance: Plants of the new *Corylus* have been observed to tolerate temperatures from about −10° C. to about 38° C. in the field in Corvallis, Oreg.

Nut yields of 'Tonda Pacifica' are similar or slightly higher than nut yields for 'Barcelona'. Since 'Tonda Pacifica' trees are smaller than 'Barcelona' trees, the nut yield efficiency for 'Tonda Pacifica' is significantly higher than that for 'Barcelona'. The nuts of 'Tonda Pacifica' are borne in clusters of 3-4 in husks 75 to 100% longer than the nuts. The husks are slit down the side and the nuts fall free at maturity. The harvest date for the nuts of 'Tonda Pacifica' is estimated to be 7-10 days before 'Barcelona'. 'Tonda Pacifica' produces fewer blank nuts and fewer defects than 'Barcelona'. Raw kernels have a moderate amount of fiber attached to the pellicle, which can be mostly removed by light roasting and rubbing. Blanching scores for 'Tonda Pacifica' are better than for 'Barcelona' and 'Tonda Gentile delle Langhe'.

Fingerprinting with microsatellite markers, also known as simple sequence repeat (SSR) markers, was performed. Twenty nine marker loci (Table 1) were selected from those published for hazelnut (Bassil et al. (2005) J. Amer. Soc. Hort. Sci., 130:543-549; Bassil et al. (2005) Acta Hort., 686:105-110; Boccacci et al. (2005) Molec. Ecol. Notes, 5:934-937; Gürcan et al. (2010) Tree Genetics and Genomes (available on-line as DOI 10.1007/s11295-010-0269-y); Gürcan et al. (2010) Molecular Breeding, 26:551-559). SSR markers have been used for fingerprinting hazelnut accessions (Boccacci et al. (2006) Genome 49:598-611; Gökirmak et al. (2009) Genetic Resources and Crop Evolution, 56:147-172; Gürcan et al. (2010) Plant Breeding, 129:422-434). Using primers designed for each SSR loci, hazelnut DNA was amplified by PCR. One of the two primers was fluorescently labeled with FAM, HEX, or NED, and the size of the amplified fragment was determined by capillary electrophoresis on an ABI 3100 instrument (Applied Biosystems; Foster City, Calif.). 'Tonda Pacifica' was found to exhibit different allele sizes at certain loci that allowed for it to be distinguish from other hazelnut genotypes such as its parent 'Tonda Gentile delle Langhe' and its grandparents 'Barcelona' and 'Extra Ghiaghli' (Table 2).

TABLE 1

Primers and annealing temperatures for the 29 microsatellite marker loci used to fingerprint 'Tonda Pacifica' and five other hazelnut cultivars.

| Locus | Tm | Allele Sizes | Repeat Motif |
|---|---|---|---|
| A613 | 60 | 149-177 | $(TC)_{13}(CA)_{12}$ |
| A614 | 60 | 125-156 | $(TC)_{17}(CA)_{10}NNN(CA)_6$ |
| A616 | 60 | 136-162 | $(AC)_{11}$ |
| A640 | 67 | 354-378 | $(CT)_{15}(CA)_{13}$ |
| B029b | 58 | 114-136 | $(GA)_{13}$ |
| B619 | 60 | 146-180 | $(TC)_{21}$ |
| B628 | 60 | 290-312 | $(TC)_7NN(CT)_6$ |
| B634 | 60 | 218-238 | $(AG)_{15}$ |
| B657 | 60 | 210-228 | $(AG)_{15}$ |
| B664 | 60 | 186-216 | $(TC)_{21}$ |
| B665 | 60 | 177-203 | $(CT)_{17}$ |
| B670 | 60 | 153-182 | $(GA)_{19}$ |
| B671 | 60 | 221-249 | $(AG)_6NN(GA)_{17}$ |
| B706 | 60 | 168-206 | $(CT)_{28}$ |
| B720 | 60 | 159-179 | $(AG)_{14}$ |
| B732 | 60 | 140-156 | $(GA)_{13}$ |
| B733 | 60 | 161-183 | $(TC)_{15}$ |
| B741 | 60 | 176-194 | $(GT)_5(GA)_{12}$ |
| B749 | 60 | 200-210 | $(TC)_{12}$ |
| B751 | 60 | 141-153 | $(GA)_{15}$ |
| B758 | 60 | 154-176 | $(CT)_{15}$ |
| B767 | 60 | 198-238 | $(TC)_{15}(AT)_7$ |
| B776 | 60 | 134-148 | $(GA)_{17}$ |
| B795 | 60 | 296-332 | $(TC)_8Ns(CT)_7Ns(CT)_{10}Ns(TC)_5$ |
| C115 | 60 | 167-225 | $(TAA)_5(GAA)_{12}$ |
| KG807 | 54 | 226-248 | $(TAAA)AA(TAAA)_2A(TAAA)_2$ |
| KG810 | 56 | 366-392 | $(AG)_{15}$ |
| KG827 | 67 | 264-282 | $(CT)_{13}AA(CA)_7$ |
| KG830 | 67 | 279-311 | $(CT)_{14}GTATT(CA)_8$ |

| Locus | Forward Primer (5'-3') (SEQ ID NO) | Reverse Primer (5'-3') (SEQ ID NO) |
|---|---|---|
| A613 | Ned-CACACGCCTTGTCACTCTTT (1) | R-CCCCTTTCACATGTTTGCTT (30) |
| A614 | Hex-TGGCAGAGCTTTGTCAGCTT (2) | R-GCAGTGGAGGATTGCTGACT (31) |
| A616 | Fam-CACTCATACCGCAAACTCCA (3) | R-ATGGCTTTTGCTTCGTTTTG (32) |
| A640 | F-TGCCTCTGCAGTTAGTCATCAAATGTAGG (4) | Fam-CGCCATATAATTGGGATGCTTGTTG (33) |
| B029b | Ned-CAATTTACACCTCAGGGAAGAG (5) | R-AAGTTCACCCAAGAAATCCAC (34) |
| B619 | Fam-AGTCGGCTCCCCTTTTCTC (6) | R-GCGATCTGACCTCATTTTTG (35) |
| B628 | Fam-AATCCCCTCTAGCCCCATTA (7) | R-CACAGAATATTTGTAATTACCACCACA (36) |
| B634 | Hex-CCTGCATCCAGGACTCATTA (8) | R-GTGCAGAGGTTGCACTCAAA (37) |
| B657 | Ned-GAGAGTGCGTCTTCCTCTGG (9) | R-AGCCTCACCTCCAACGAAC (38) |
| B664 | Ned-CAAAGCCGTCGACAACAG (10) | R-TTTGCATTTGATGCCGATAA (39) |
| B665 | Hex-GCAACCACCAAATTGCACTA (11) | R-GCTTTTAAAGTCCACGCATGA (40) |
| B670 | Fam-CAACACTCACGTTTGGTTGC (12) | R-TCTGTGTTGTTGGGAGTGGA (41) |
| B671 | Hex-TTGCCAGTGCATACTCTGATG (13) | R-ACCAGCTCTGGGCTTAACAC (42) |
| B706 | Fam-TGCATGAAATGGAATCACAGA (14) | R-AGCAAAGAGGTAAGCAAATTCA (43) |
| B720 | Fam-CTCTGTGTCGGCTTTCTGGT (15) | R-ATAAACCTCACGCCACACCT (44) |
| B732 | Fam-GCCCTTCTTCTTTTCTGCAA (16) | R-AGTGCCACCTCAACAAATCC (45) |
| B733 | Ned-CACCCTCTTCACCACCTCAT (17) | R-CATCCCCTGTTGGAGTTTTC (46) |
| B741 | Fam-GTTCACAGGCTGTTGGGTTT (18) | R-CGTGTTGCTCATGTGTTGTG (47) |
| B749 | Hex-GGCTGACAACACAGCAGAAA (19) | R-TCGGCTAGGGTTAGGGTTTT (48) |
| B751 | Fam-AGCTGGTTCTTCGACATTCC (20) | R-AAACTCAAATAAAACCCCTGCTC (49) |
| B758 | Fam-TAATTTAAGCTGCCGTGCAA (21) | R-TGCAAAATTGCATTGCTCAT (50) |
| B767 | Fam-CCACCAACTGTTTCACACCA (22) | R-GCGAAATGGAGCTCTTGAAC (51) |
| B776 | Fam-TGTATGTACACACGGAGAGAGAGA (23) | R-TGAGGGGAAGAGGTTTGATG (52) |
| B795 | Fam-GACCCACAAACAATAACCTATCTC (24) | R-TGGGCATCATCCAGGTCTA (53) |
| C115 | Fam-CATTTTCCGCAGATAATACAGG (25) | R-TCCAGATCTGCCTCCATATAAT (54) |
| KG807 | AAGCAAGAAAGGGATGGT(26) | Fam-CTTACAGATAAATGGCTCAAA (55) |
| KG810 | TCCTCACCAATCACACTATTT (27) | Ned-TTATTCCACCAAAGTCTACCTC (56) |
| KG827 | Fam-AGAACTCCGACTAATAATCCTAACCCTTGC (28) | R-GAGGGAGCAAGTCAAAGTTGAGAAGAAA (57) |
| KG830 | Ned-TGGAGGAAGTTTTGAATGGTAGTAGAGGA (29) | R-AAAGCAACTCATAGCTGAAGTCCAATCA (58) |

Tm = annealing temperature.

One of the two primers at each locus had a fluorescent label (Fam, Hex or Ned) to allow sizing with capillary electrophoresis.

TABLE 2

Allele sizes in 'Tonda Pacifica' and five other hazelnut cultivars at 29 microsatellite loci. The female parent of 'Tonda Pacifica' is 'Tonda Gentile delle Langhe'. The male parent is OSU 23.024, which is from a cross of 'Barcelona' x 'Extra Ghiaghli'. Note that one of the alleles of 'Tonda Pacifica' is from 'Tonda Gentile delle Langhe', and the other is from either 'Barcelona' or 'Extra Ghiaghli'.

| | Cultivar | | | | | |
|---|---|---|---|---|---|---|
| Micro-satellite Locus | Tonda Pacifica | Tonda Gentile delle Langhe | Barcelona | Extra Ghiaghli | Clark | Lewis |
| A613 | 157/167 | 151/157 | 151/159 | 167/169 | 151/177 | 151/177 |
| A614 | 134/148 | 125/134 | 125/131 | 125/148 | 131/131 | 131/148 |
| A616 | 148/158 | 148/150 | 142/150 | 150/158 | 148/150 | 148/150 |
| A640 | 368/374 | 354/368 | 354/374 | 374/374 | 354/354 | 354/354 |
| B029b | 118/120 | 120/124 | 124/130 | 118/132 | 124/130 | 124/124 |
| B619 | 164/170 | 148/164 | 156/170 | 164/174 | 156/168 | 156/168 |
| B628 | 297/297 | 297/299 | 293/297 | 293/297 | 297/297 | 293/297 |
| B628 | 298/298 | 298/300 | 294/298 | 294/298 | 298/298 | 294/298 |
| B634 | 226/226 | 226/226 | 226/226 | 226/226 | 230/234 | 226/234 |
| B657 | 210/226 | 218/226 | 218/222 | 210/222 | 210/218 | 214/222 |
| B664 | 186/206 | 186/206 | 206/214 | 206/208 | 192/204 | 188/208 |
| B665 | 178/185 | 185/189 | 189/195 | 178/189 | 195/195 | 193/195 |
| B670 | 169/182 | 159/182 | 153/159 | 169/177 | 173/177 | 159/173 |
| B671 | 227/237 | 237/241 | 223/227 | 227/247 | 223/247 | 223/223 |
| B706 | 174/206 | 190/206 | 168/190 | 172/174 | 190/200 | 190/200 |
| B720 | 161/167 | 167/167 | 161/167 | 165/179 | 159/159 | 159/179 |

TABLE 2-continued

Allele sizes in 'Tonda Pacifica' and five other hazelnut cultivars at 29 microsatellite loci. The female parent of 'Tonda Pacifica' is 'Tonda Gentile delle Langhe'. The male parent is OSU 23.024, which is from a cross of 'Barcelona' x 'Extra Ghiaghli'. Note that one of the alleles of 'Tonda Pacifica' is from 'Tonda Gentile delle Langhe', and the other is from either 'Barcelona' or 'Extra Ghiaghli'.

| | Cultivar | | | | | |
|---|---|---|---|---|---|---|
| Micro-satellite Locus | Tonda Pacifica | Tonda Gentile delle Langhe | Barcelona | Extra Ghiaghli | Clark | Lewis |
| B732 | 140/154 | 140/154 | 150/154 | 140/154 | 150/154 | 150/150 |
| B733 | 171/173 | 171/173 | 171/173 | 171/171 | 171/179 | 173/179 |
| B741 | 176/186 | 176/184 | 176/186 | 176/184 | 176/186 | 176/186 |
| B749 | 206/208 | 206/208 | 208/208 | 208/208 | 208/208 | 206/208 |
| B751 | 143/153 | 149/153 | 143/153 | 143/147 | 147/151 | 151/153 |
| B758 | 160/160 | 160/168 | 168/168 | 160/160 | 168/168 | 168/168 |
| B767 | 198/216 | 211/216 | 211/237 | 198/204 | 204/235 | 211/235 |
| B776 | 136/136 | 136/136 | 134/136 | 134/136 | 136/136 | 136/136 |
| B795 | 312/330 | 312/330 | 330/330 | 296/310 | 330/330 | 330/330 |
| C115 | 173/182 | 173/173 | 193/193 | 182/193 | 193/193 | 193/193 |
| KG807 | 246/248 | 234/248 | 234/248 | 248/250 | 226/248 | 234/248 |
| KG810 | 378/382 | 374/378 | 374/378 | 378/382 | 378/380 | 378/382 |
| KG827 | 268/282 | 268/268 | 280/282 | 276/282 | 270/276 | 270/280 |
| KG830 | 291/295 | 291/295 | 291/295 | 289/295 | 295/303 | 291/303 |

SEQUENCE LISTING

```
<160> NUMBER OF SEQ ID NOS: 58

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1

cacacgcctt gtcactcttt                                                20


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

tggcagagct ttgtcagctt                                                20


<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3

cactcatacc gcaaactcca                                                20


<210> SEQ ID NO 4
<211> LENGTH: 29
<212> TYPE: DNA
```

-continued

<213> ORGANISM: Artificial Sequence
<220> FEATURE:
<223> OTHER INFORMATION: Primer

<400> SEQUENCE: 4 tgcctctgca gttagtcatc aaatgtagg 29

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5 caatttacac ctcagggaag ag 22

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6 agtcggctcc ccttttctc 19

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7 aatcccctct agccccatta 20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8 cctgcatcca ggactcatta 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9 gagagtgcgt cttcctctgg 20

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10

-continued caaagccgtc gacaacag 18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11 gcaaccacca aattgcacta 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12 caacactcac gtttggttgc 20

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13 ttgccagtgc atactctgat g 21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14 tgcatgaaat ggaatcacag a 21

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15 ctctgtgtcg gctttctggt 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16 gcccttcttc ttttctgcaa 20

<210> SEQ ID NO 17
<211> LENGTH: 20
<212> TYPE: DNA

-continued

<213> ORGANISM: Artificial Sequence
<220> FEATURE:
<223> OTHER INFORMATION: Primer

<400> SEQUENCE: 17 caccctcttc accacctcat 20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18 gttcacaggc tgttgggttt 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19 ggctgacaac acagcagaaa 20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20 agctggttct tcgacattcc 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21 taatttaagc tgccgtgcaa 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22 ccaccaactg tttcacacca 20

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23

-continued tgtatgtaca cacggagaga gaga 24

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24 gacccacaaa caataaccta tctc 24

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25 cattttccgc agataataca gg 22

<210> SEQ ID NO 26
<211> LENGTH: 18
<212> TYPE: DNA
<213> ORGANISM: Artificial Sequence
<220> FEATURE:
<223> OTHER INFORMATION: Primer

<400> SEQUENCE: 26 aagcaagaaa gggatggt 18

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27 tcctcaccaa tcacactatt t 21

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28 agaactccga ctaataatcc taacccttgc 30

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29 tggaggaagt tttgaatggt agtagagga 29

<210> SEQ ID NO 30
<211> LENGTH: 20
<212> TYPE: DNA

-continued

<213> ORGANISM: Artificial Sequence
<220> FEATURE:
<223> OTHER INFORMATION: Primer

<400> SEQUENCE: 30 ccccttttcac atgtttgctt 20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31 gcagtggagg attgctgact 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32 atggcttttg cttcgttttg 20

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33 cgccatataa ttgggatgct tgttg 25

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34 aagttcaccc aagaaatcca c 21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35 gcgatctgac ctcatttttg 20

<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36

-continued cacagaatat ttgtaattac caccaca 27

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37 gtgcagaggt tgcactcaaa 20

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38 agcctcacct ccaacgaac 19

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39 tttgcatttg atgccgataa 20

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40 gcttttaaag tccacgcatg a 21

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41 tctgtgttgt tgggagtgga 20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42 accagctctg ggcttaacac 20

<210> SEQ ID NO 43
<211> LENGTH: 22
<212> TYPE: DNA

-continued

<213> ORGANISM: Artificial Sequence
<220> FEATURE:
<223> OTHER INFORMATION: Primer

<400> SEQUENCE: 43 agcaaagagg taagcaaatt ca 22

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44 ataaacctca cgccacacct 20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45 agtgccacct caacaaatcc 20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46 catcccctgt tggagttttc 20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47 cgtgttgctc atgtgttgtg 20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48 tcggctaggg ttagggtttt 20

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49

-continued aaactcaaat aaaacccctg ctc 23

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50 tgcaaaattg cattgctcat 20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51 gcgaaatgga gctcttgaac 20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52 tgaggggaag aggtttgatg 20

<210> SEQ ID NO 53
<211> LENGTH: 19
<212> TYPE: DNA
<213> ORGANISM: Artificial Sequence
<220> FEATURE:
<223> OTHER INFORMATION: Primer

<400> SEQUENCE: 53 tgggcatcat ccaggtcta 19

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54 tccagatctg cctccatata at 22

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55 cttacagata aatggctcaa a 21

<210> SEQ ID NO 56
<211> LENGTH: 22
<212> TYPE: DNA

-continued

```
<213> ORGANISM: Artificial Sequence
<220> FEATURE:
<223> OTHER INFORMATION: Primer

<400> SEQUENCE: 56

ttattccacc aaagtctacc tc                                          22


<210> SEQ ID NO 57
<211> LENGTH: 28
<212> TYPE: DNA
<213> ORGANISM: Artificial Sequence
<220> FEATURE:
<223> OTHER INFORMATION: Primer

<400> SEQUENCE: 57

gagggagcaa gtcaaagttg agaagaaa                                    28


<210> SEQ ID NO 58
<211> LENGTH: 28
<212> TYPE: DNA
<213> ORGANISM: Artificial Sequence
<220> FEATURE:
<223> OTHER INFORMATION: Primer

<400> SEQUENCE: 58

aaagcaactc atagctgaag tccaatca                                    28
```

What is claimed is:

1. A new and distinct *Corylus* plant named 'Tonda Pacifica' as illustrated and described.

* * * * *

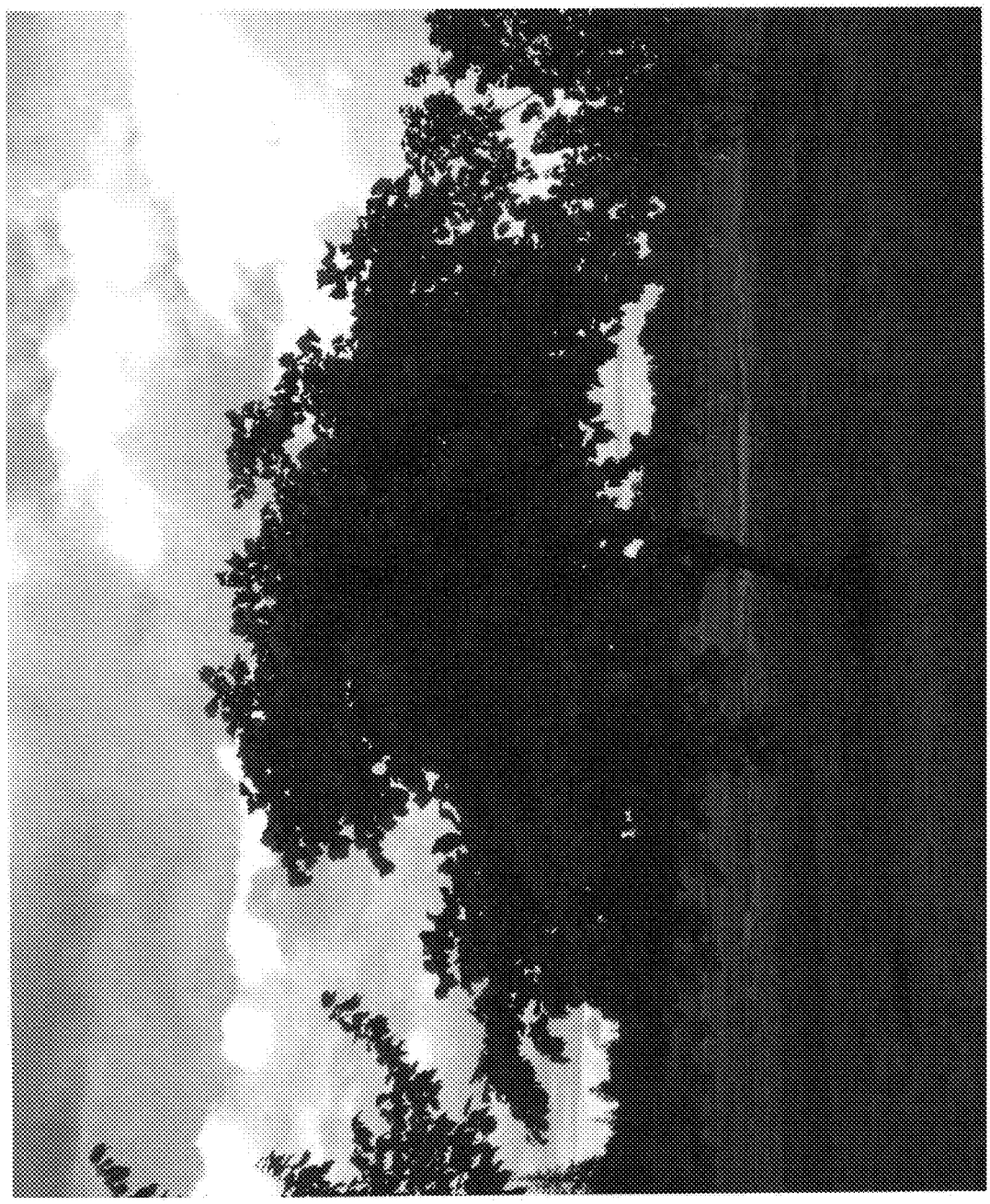

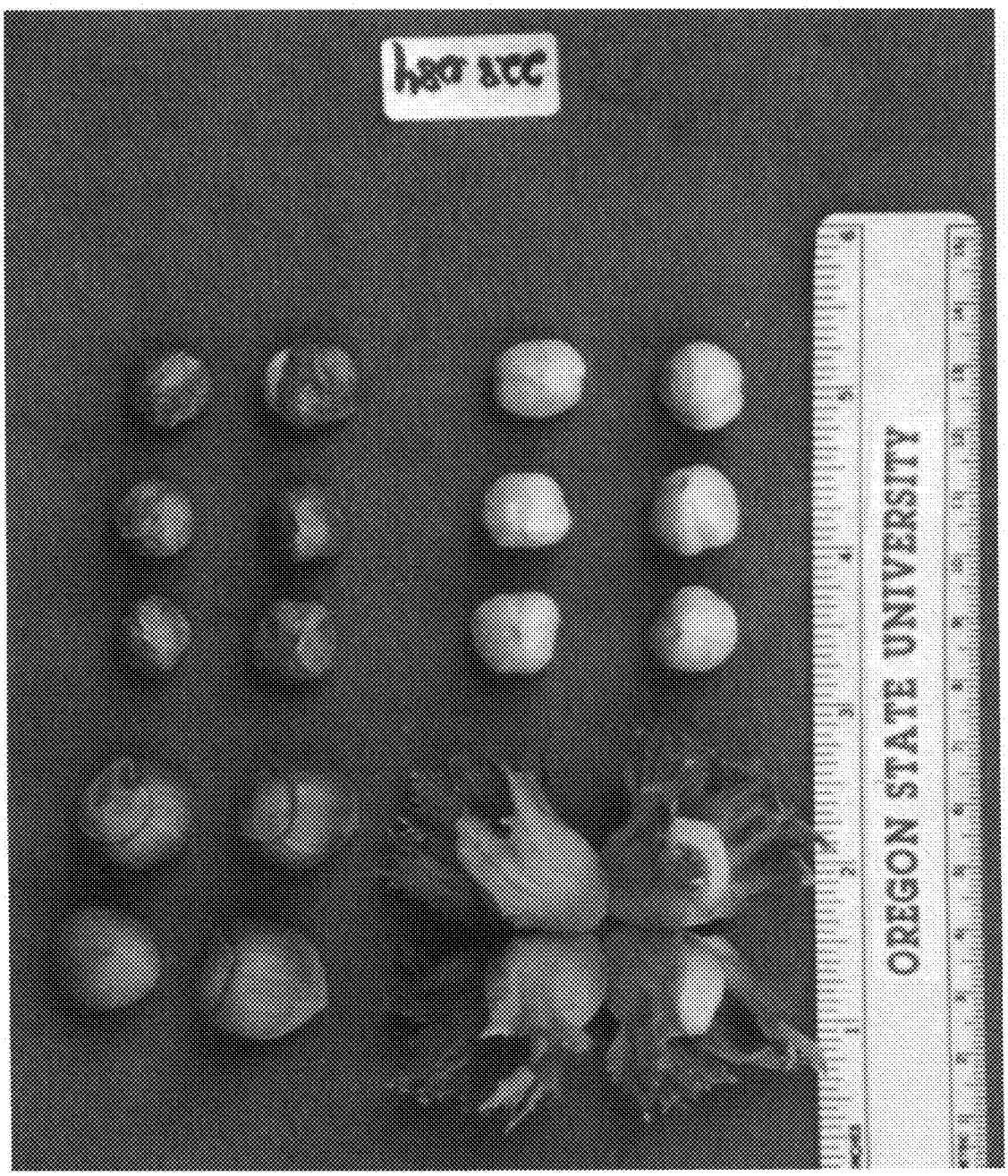
OREGON STATE UNIVERSITY